United States Patent [19]

Pelosi, Jr.

[11] 4,002,659
[45] Jan. 11, 1977

[54] ETHYL 2',5'-DICHLORO-4'-THIOCYANATOFUMARANILATE

[75] Inventor: Stanford S. Pelosi, Jr., Norwich, N.Y.

[73] Assignee: Morton-Norwich Products, Inc., Norwich, N.Y.

[22] Filed: Jan. 16, 1976

[21] Appl. No.: 649,584

[52] U.S. Cl. .............................. 260/454; 424/302
[51] Int. Cl.² ...................................... C07C 161/02
[58] Field of Search .................................. 260/454

[56] References Cited

UNITED STATES PATENTS

| 3,305,575 | 2/1967 | Debarre et al. ............... 260/454 |
| 3,455,982 | 7/1969 | Watanabe et al. ............. 260/454 |
| 3,455,985 | 7/1969 | Sternbach ..................... 260/454 |

OTHER PUBLICATIONS

Wagner, (Synthetic Organic Chemistry), p. 566.

*Primary Examiner*—Lewis Gotts
*Assistant Examiner*—D. R. Phillips
*Attorney, Agent, or Firm*—Anthony J. Franze

[57] ABSTRACT

Ethyl 2',5'-dichloro-4'-thiocyanatofumaranilate is an effective antibacterial agent.

1 Claim, No Drawings

ETHYL 2',5'-DICHLORO-4'-THIOCYANATOFUMARANILATE

This invention relates to the compound ethyl 2',5'-dichloro-4'-thiocyanatofumaranilate of the formula:

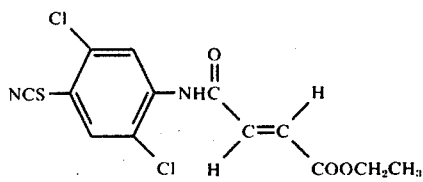

and a method for its preparation.

The compound of this invention possesses antibacterial activity. It is particularly inimical to *Staphylococcus aureus*, *Escherichia coli*, and *Hemophilus vaginalis* in the commonly employed in vitro technique for determining antibacterial activity at levels of from 6.25 to 12.5 mcg of compound per milliliter of test media. It is thus adapted to be combined in various forms such as ointments, powders, solutions, sprays, dusts and the like in a concentration of from 0.1 – 1% by weight suitable for application to prevent bacterial contamination.

The compound of this invention is readily prepared. Currently it is preferred to react 2,5-dichloro-4-thiocyanatoaniline with ethyl fumaroyl chloride.

In order that this invention may be fully available to and understood by those skilled in the art, the method now preferred is briefly described.

Ethyl 2',5'-dichloro-4'-thiocyanatofumaranilate

Ethyl fumaroyl chloride (39 g, 0.24 mole) was added dropwise over 15 min to a stirred, refluxing mixture of 48 g (0.22 mole) of 2,5-dichloro-4-thiocyanatoaniline and 48 g (0.35 mole) of anhydrous $K_2CO_3$ in 250 ml of dry acetone. The mixture was heated under reflux for 5 hr and allowed to stand overnight. The solvent was removed on a rotary evaporator. The solid residue was stirred in water, collected by filtration, and recrystallized from ethanol to give 46 g (60%) of product. Two additional recrystallizations from ethanol give an analytical sample, m.p. 148°–152°.

Anal. Calcd. for $C_{13}H_{10}Cl_2N_2O_3S$: C, 45.23; H, 2.92; N, 8.11. Found: C, 44.83; H, 2.97; N, 8.06.

What is claimed is:
1. The compound ethyl 2',5'-dichloro-4'-thiocyanatofumaranilate.